(12) United States Patent
Tonner (10) Patent No.: US 12,128,254 B2
(45) Date of Patent: Oct. 29, 2024

(54) MULTI-SPECTRAL FLUORESCENCE FOR IN-VIVO DETERMINATION OF PROTON ENERGY AND RANGE IN PROTON THERAPY

(71) Applicant: H. LEE MOFFITT CANCER CENTER AND RESEARCH INSTITUTE, INC., Tampa, FL (US)

(72) Inventor: Brian P. Tonner, Winter Springs, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 18/531,960

(22) Filed: Dec. 7, 2023

(65) Prior Publication Data

US 2024/0100362 A1     Mar. 28, 2024

Related U.S. Application Data

(60) Division of application No. 17/148,531, filed on Jan. 13, 2021, now Pat. No. 11,878,186, which is a continuation of application No. 14/413,033, filed as application No. PCT/US2013/052563 on Jul. 29, 2013, now abandoned.

(Continued)

(51) Int. Cl.
    *A61N 5/10*         (2006.01)
    *A61B 6/50*         (2024.01)
    *A61B 6/58*         (2024.01)

(52) U.S. Cl.
    CPC ......... *A61N 5/1049* (2013.01); *A61N 5/1048* (2013.01); *A61N 5/1064* (2013.01); *A61B 6/508* (2013.01); *A61B 6/583* (2013.01); *A61N 2005/1051* (2013.01);

(Continued)

(58) Field of Classification Search
    CPC .. A61N 5/1049; A61N 5/1048; A61N 5/1064; A61N 5/1071; A61N 2005/1051; A61N 2005/1059; A61N 2005/1087; A61B 6/508; A61B 6/583
    See application file for complete search history.

(56) References Cited

U.S. PATENT DOCUMENTS

| | | | |
|---|---|---|---|
| 6,219,403 B1 * | 4/2001 | Nishihara | A61N 5/1048 378/65 |
| 6,778,850 B1 * | 8/2004 | Adler | A61B 90/10 378/4 |

(Continued)

*Primary Examiner* — Bo Joseph Peng
(74) *Attorney, Agent, or Firm* — Meunier Carlin & Curfman LLC (57) ABSTRACT

The accuracy charged-particle beam trajectories used for radiation therapy in patients is improved by providing feedback on the beam location within a patient's body or a quality assurance phantom. Particle beams impinge on a patient or phantom in an arrangement designed to deliver radiation dose to a tumor, while avoiding as much normal tissue as can be achieved. By placing fiducial markers in the tumor or phantom that contain specific atomic constituents, a detection signal consisting of atomic fluorescence is produced by the particle beam. An algorithm can combine the detected fluorescence signal with the known location of the fiducial markers to determine the location of the particle beam in the patient or phantom.

12 Claims, 6 Drawing Sheets

Related U.S. Application Data

(60) Provisional application No. 61/676,673, filed on Jul. 27, 2012.

(52) U.S. Cl.
CPC .... *A61N 2005/1059* (2013.01); *A61N 5/1071* (2013.01); *A61N 2005/1087* (2013.01)

(56) References Cited

U.S. PATENT DOCUMENTS

| | | | |
|---|---|---|---|
| 2005/0080332 A1* | 4/2005 | Shiu | A61B 6/032 |
| | | | 600/417 |
| 2005/0209533 A1* | 9/2005 | Lorenz | A61M 25/0905 |
| | | | 604/528 |
| 2007/0295910 A1* | 12/2007 | Harada | A61N 5/1049 |
| | | | 250/354.1 |
| 2008/0067401 A1* | 3/2008 | Harada | G21K 5/04 |
| | | | 250/396 R |
| 2008/0312528 A1* | 12/2008 | Bertolina | A61B 34/20 |
| | | | 600/426 |
| 2009/0238325 A1* | 9/2009 | Kargar | A61B 6/488 |
| | | | 378/8 |
| 2010/0034352 A1* | 2/2010 | Aoi | A61N 5/1048 |
| | | | 378/65 |
| 2011/0013752 A1* | 1/2011 | Takahashi | A61B 6/588 |
| | | | 378/205 |

* cited by examiner

MULTI-SPECTRAL FLUORESCENCE FOR IN-VIVO DETERMINATION OF PROTON ENERGY AND RANGE IN PROTON THERAPY

CROSS-REFERENCE TO RELATED APPLICATIONS

This application is a divisional of U.S. patent application Ser. No. 17/148,531, filed Jan. 13, 2021, which is a continuation of U.S. patent application Ser. No. 14/413,033, filed Jan. 6, 2015, which is a national stage application filed under 35 U.S.C. 371 of PCT/US2013/052563, filed Jul. 29, 2013, which the claims benefit of and priority to U.S. Provisional Patent App. No. 61/676,673, filed Jul. 27, 2012, all of which are incorporated herein by reference in their entireties.

TECHNICAL FIELD

The disclosure relates to a method and apparatus for improving the accuracy of delivery of charged-particle beams for the treatment of cancer. The disclosure also includes an improved method for performing quality-assurance measurements on charged-particle beams used in therapy.

BACKGROUND

Charged-particle beams are among the most advanced methods currently available for the treatment of cancer tumors by radiotherapy. The more common charged-particle beam therapy centers use protons as the particle of choice, while a few centers have begun using heavy ion particles such as carbon ion beams.

The specific advantage of charged-particle beam therapy in treating tumors is the physical effect known as the "Bragg peak." The Bragg peak is a sharp increase in delivered dose, which occurs near the end of a particle trajectory in the patient. The physical characteristics of the Bragg peak make it possible, in principle, to more carefully conform the particle-beam to the shape of the tumor. In addition, since there is very little beam intensity beyond the range of the Bragg peak, there can be significant reduction in overall radiation dose to normal tissue, as compared to photon external beam radiotherapy.

In order to make use of narrow tumor margins that are possible in principle with charged particle beams, it is necessary to have an accurate knowledge of the beam penetration in the patient. The current practice is to infer the penetration of charged particles, based on information gathered from x-ray imagery, particularly computed tomography (CT). However, there are well-known problems with making the extrapolation from CT imagery to the expected penetration of charged particle beams, which leads to an uncertainty in the knowledge of the beam penetration in the actual patient. In addition, the patient anatomy can change over time, leading to changes in the actual penetration of the charged particle beam from one treatment to the next, further leading to uncertainty in the knowledge of the actual delivered dose to tumor and to normal tissue.

SUMMARY

The disclosed systems, methods, and devices address the uncertainty in beam location by providing a means to determine particle beam penetration in a patient during the time frame of a daily treatment. The disclosed systems, methods, and devices may also be used to determine the charged particle beam penetration in phantoms constructed from materials chosen to mimic the behavior of human tissue when exposed to radiation, often called "water-equivalent" materials. The disclosed systems, methods, and devices improve the accuracy of determination of charged particle beam penetration in patients. The disclosed apparatus and methods also apply to the calibration of charged particle beams for therapeutic use. This disclosure applies to all charged-particle beam therapies for treating cancer.

Disclosed are a system, method, and apparatus that provide information about the trajectory of a charged particle beam as it traverses a patient undergoing external beam therapy. Although the present embodiment primarily addresses proton beam therapy, it is also applicable to other charged particle beams, and specifically to carbon atom beams.

A method is disclosed for determining charged-particle beam trajectories through the use of a variation of the charged-particle beam energy as a function of time, and measurement of the yield of fluorescent radiation from fiducial markers as a function of time, and application of an algorithm to extract information on the beam trajectory. A "fiducial marker" as used herein includes any material with a known composition that is placed at a known location. In particular, the fiducial marker can contain a material with x-ray fluorescence.

Also disclosed is a method to use a charged-particle beam in a way that is compatible with its use for patient therapy. The charged-particle beam excites atomic electrons in all of the materials along the charged-particle beam path. These excited electrons leave behind an atom in an excited energy state, which is de-excited through a number of processes. One of the processes is the production of fluorescent x-rays.

The method detects these fluorescent x-rays, and uses the intensity of the fluorescence, along with other information, to determine the trajectory of the charged-particle beam in the patient. The energy of the fluorescent x-ray can be selected such that the x-ray can readily pass through the patient's tissue and reach the detector. For example, the energy of the fluorescent x-ray can be at least 20 keV (e.g., at least 30 keV, at least 40 keV, at least 50 keV, at least 60 keV, at least 70 keV, at least 80 keV, at least 90 keV, at least 100 keV, at least 110 keV, at least 120 keV, at least 130 keV, or at least 140 keV). In some embodiments, the energy of the fluorescent x-ray can be 150 keV or less (e.g., 140 keV or less, 130 keV or less, 120 keV or less, 110 keV or less, 100 keV or less, 90 keV or less, 80 keV or less, 70 keV or less, 60 keV or less, 50 keV or less, 40 keV or less, or 30 keV or less). The energy of the fluorescent x-ray can range from any of the minimum energies described above to any of the maximum energies described above. For example, the energy of the fluorescent x-ray can range from 20 keV to 150 keV (e.g., from 20-40 keV, from 40-50 keV, from 50-60 keV, from 60-80 keV, or from 60-90 keV).

By using fluorescent x-rays, the method takes advantage of the narrow line-width and high detection efficiency of x-rays of atomic origin. The line-width of the fluorescent x-ray can be sufficiently narrow, such that the fluorescent x-ray can be readily detected without interference from a wide range of x-rays from other processes that do not provide beam position information. Suitable line-widths for the fluorescent x-ray line-width can be selected in view of the detector or detectors configured to measure the fluorescent x-ray. For example, the line-width of fluorescence x-rays can be approximately 100 eV for high-resolution solid-state detectors, or a few hundred eV for proportional counters. In certain embodiments, the line-width of the fluorescent x-ray is 1 keV or less (e.g., 900 eV or less, 800 eV or less, 700 eV or less, 600 eV or less, 500 eV or less, 400 eV or less, 300 eV or less, 300 eV or less, or 100 eV or less). The line-width of the fluorescent x-ray can be sufficiently narrow to permit the separation of lines from different elements and/or different inner-shell atomic energy levels, such as the K and L shell of the element gold (Au).

A number of materials can be selected to create fiducial markers that will produce fluorescent x-rays that will pass through the body with low attenuation but have a high detection efficiency. The fluorescent x-ray is produced by atomic de-excitation. The chemical element used as a fiducial marker can be selected to be compatible with human use and with radiotherapy. In some embodiments, the method uses gold (Au) fiducial markers, which produce K-shell fluorescent x-rays of an energy and line-width of 60-80 keV, which is suitable for detection during clinical procedures. Other atomic elements can also produce suitable x-rays, and the use of these other elements is included in the scope of the invention. Suitable materials for producing these fluorescent x-rays include materials used commonly in medicine and as contrast agents, including gold (Au), gadolinium (Gd, with K shell transition radiation in the range of 42-50 keV), iridium (Ir, with K shell transition radiation in the range of 63-76 keV), iodine (I, with K shell transition radiation in the range of 28-33 keV), xenon (Xe, with K shell transition radiation in the range of 29-33 keV), barium (Ba, with K shell transition radiation in the range of 32-36 keV), lanthanum (La, with K shell transition radiation in the range of 33-38 keV), samarium (Sm, with K shell transition radiation in the range of 40-45 keV), europium (Eu, with K shell transition radiation in the range of 41-47 keV), terbium (Tb, with K shell transition radiation in the range of 44-50 keV), erbium (Er, with K shell transition radiation in the range of 48-56 keV), thulium (Tm, with K shell transition radiation in the range of 50-58 keV), lutetium (Lu, with K shell transition radiation in the range of 53-61 keV), tungsten (W, with K shell transition radiation in the range of 58-67 keV), rhenium (Re, with K shell transition radiation in the range of 58-69 keV), osmium (Os, with K shell transition radiation in the range of 61-71 keV), and Platinum (Pt, with K shell transition radiation in the range of 65-76 keV).

The method uses a known position of fiducial markers to identify the emission location of fluorescent x-rays. Implanted fiducial markers are common in radiotherapy, and specific examples are for prostate therapy and lung therapy. However, implanted fiducials can be used in many other areas of the body for other types of cancer treatment, and these uses are included herein.

Fiducial markers are typically located by performing a computed-tomography (CT) scan of the patient, which can also be used with the disclosed methods. However, other means to locate fiducial markers that can be used in the disclosed methods include high resolution sonography, radiography, and RF emission from markers with transmitters.

Fiducial markers can take different physical forms, including metallic wires, helical coils, and surgical clips. For example, fiducial markers commonly used in medical practice for marking tumor locations, such as the Visicoil™ product and surgical clips made from gold can be used. In addition to these common fiducial markers, the method incorporates the use of other suitable classes of fiducial markers which contain x-ray fluorescent atoms, such as nanoparticles, metal-conjugated proteins, and imaging contrast agents. For example, fiducial markers may also take the form of injected liquids containing atoms that fluoresce in the energy ranges described above (e.g., emit a fluorescent x-ray having an energy of from 20-150 keV). Examples of such injectable fiducial markers includes nanoparticles formed from a suitable x-ray fluorescing material (e.g., gold nanoparticles, gadolinium nanoparticles, gold-gadolinium nanoparticles, core-shell nanoparticles containing a suitable x-ray fluorescing material in the core and a shell formed from a passivating material such as a polymer), microcontainers encapsulating a solution of a suitable x-ray fluorescing material (e.g., polymer tubes or capsules filled with, for example, a gadolinium solution), and radium containing radiopharmaceuticals.

The method uses a particular protocol for delivering the particle beam at any time prior to, during, or after treatment of a patient, in order to determine the trajectory of the beam within the patient. The particle beam is delivered with a known beam energy, which is varied, while measuring fluorescence emission from implanted fiducial marker(s) in synchrony with the variation of the beam energy. The variation of the beam energy produces a change in the depth of penetration of the charged particle beam, which is reflected in a variation of the detected fluorescence emission.

In some embodiments, the method involves the detection of an x-ray of a single energy. Attenuation of the emitted fluorescent beam can in some embodiments be affected by variations in the patient's body thickness and composition, which may not be independently determinable. Therefore, in other embodiments, the method uses the simultaneous detection of x-rays of two or more different energies. These x-rays originate at the same location in the patient. Since the x-rays have two different energies, they will travel through the patient's body with different levels of attenuation. The two (or more) x-ray energies will be detected by an energy selective x-ray detector. A suitable method for this detection is a pulse-height analysis system, such as a silicon or germanium detector, or in some cases, a scintillation counter system. Other methods of detecting the number of x-rays emitted within each energy channel are known, and may be used in the disclosed systems, methods, and devices.

By simultaneously detecting x-rays of more than one energy, it is possible to determine the ratio of the intensity of these beams that are detected. The method will work with two or more beams. In some embodiments, the K-α (near 80 keV, also called KN radiation) and K-β shell fluorescence (near 68 keV, also called KL radiation) from Au (gold) fiducials is used. However, other materials are suitable for this purpose, including in certain cases materials that occur naturally in the human body. Materials commonly used in medicine such as gadolinium, iodine, iridium, and radium have suitable energy levels that are separated by several keV and can be distinguished by suitable detectors, including solid-state detectors.

Both of the x-ray beams, e.g., K-α and K-β, pass through the same regions of the patient. Each individually experiences intensity attenuation that is a function of the energy of the x-ray beam. The energy of the beam is measured. The energy of the x-ray beam identifies the type of the beam, e.g., that it is a K-α or an K-β shell beam. With the knowledge of the type of beam, e.g., K-α or K-β shell, the ratio of the intensity of these beams can then be used to determine the attenuation thickness of the patient that the beams have traversed. This is accomplished by using a formula for x-ray attenuation based on an exponential function, in which the effective thickness of the material traversed is multiplied by the attenuation coefficient for the specific beam, e.g., the K-α or K-β shell. The attenuation coefficients can either be taken from widely known tabulated information, or determined more specifically by measurements on so-called "phantom" materials selected to mimic human tissue. The relative intensity of the beams is used with the knowledge of the exponential attenuation law to correct the information of x-ray intensity that is used to determine the proton energy and range.

The disclosed method can incorporate an algorithm for determining particle beam trajectory based on the synchronous variation of incident particle beam energy and fluorescence emission intensity. The disclosed method may also be used to adapt a therapeutic particle-beam therapy based on information revealed by application of the disclosed method, so as to improve the conformality of the particle-beam and the tumor being treated.

Energy detectors (e.g., multi-energy detectors) may be arranged at various locations around the patient to increase the number of beams that are measured, thereby reducing the time needed to complete a measurement, and to increase the accuracy of the measurement. Fluorescence x-rays may also be measured over a substantial part of the spherical solid-angle surrounding the fiducial markers using wide-angle detectors, so as to increase signal detection efficiency and reduce patient dose. As a beneficial alternative, the method allows for the use of collimated detectors in an angular arrangement, so as to determine the location of emission of fluorescence x-rays without the need for other determination of their position.

An apparatus and system are disclosed that comprise a source of charged-particles with an energy that can be varied as a function of time, fiducial markers with a constituent material that produces a fluorescence signal suitable for detection at a distance removed from the treatment field, an arrangement of detectors to measure the fluorescence signal as a function of time, and suitable computer control and electronic equipment to implement the method and apply the disclosed algorithm to extract and display information on the charged-particle beam trajectory.

The apparatus and system can incorporate a therapeutic charged-particle beam with an energy that is varied. Typically this is accomplished with a "modulation wheel", also called a "propeller". Implanted fiducial markers containing a high density of atoms of the desired element to produce fluorescence x-rays may be placed in or near the tumor treatment location. Fluorescence detectors may be arranged outside the patient so as to be outside the path of the incident particle beam, but are otherwise located close to the patient's skin surface to enhance signal detection.

Fluorescence signals may be measured from the detectors, and selected according to their energy using pulse-height discrimination techniques. The energy of fluorescence can be determined by the element used in the fiducial implant. This energy may be high enough so that large numbers of x-rays are transmitted outside the patient. By using fiducial markers of the heavy element gold (Au), the marker is compatible with clinical use, and the fluorescence x-ray is well-separated from other sources of background radiation.

A computer system can be used to record the intensity of emitted x-rays while monitoring the energy of the incident particle beam. An algorithm, e.g., derived from Monte-Carlo simulations, can be used to extract beam trajectory from the measured emission intensity patterns.

An imaging detection system may be used to create a spatial map of the location of the emitted fluorescent x-rays, so as to more accurately determine the location of protons that create the fluorescence. This spatial imaging detection system may be capable of sorting fluorescent x-rays according to their energy, and to use this information for attenuation correction as described above.

Also disclosed are method of treating cancer in a subject that involve implanting fiducial markers in or near the cancer, determining charged-particle beam trajectories through the use of a variation of the charged-particle beam energy as a function of time, measurement of the yield of fluorescent radiation from the fiducial markers as a function of time, using an algorithm to optimize beam trajectory, and using the optimized charged-particle beam to irradiate the cancer. Any cancer, e.g., solid tumor, that can be treated by charged-particle beam radiotherapy can be treated by this optimized method. For example, the cancer can be lung, prostate, breast, skull base tumors, or uveal melanomas.

The details of one or more embodiments of the invention are set forth in the accompanying drawings and the description below. Other features, objects, and advantages of the invention will be apparent from the description and drawings, and from the claims.

DETAILED DESCRIPTION

In the following description, reference is made to the accompanying drawings, which form a part hereof, and which show, by way of illustration, specific examples or processes in which the invention may be practiced. Where possible, the same reference numbers are used throughout the drawings to refer to the same or like components. In some instances, numerous specific details are set forth in order to provide a thorough understanding of the invention. The invention, however, may be practiced without the specific details or with certain alternative equivalent devices and/or components and methods to those described herein. In other instances, well-known methods and devices and/or components have not been described in detail so as not to unnecessarily obscure aspects of the invention. For the sake of clarity, the various elements represented in the figures are not necessarily to scale.

Figure 1:
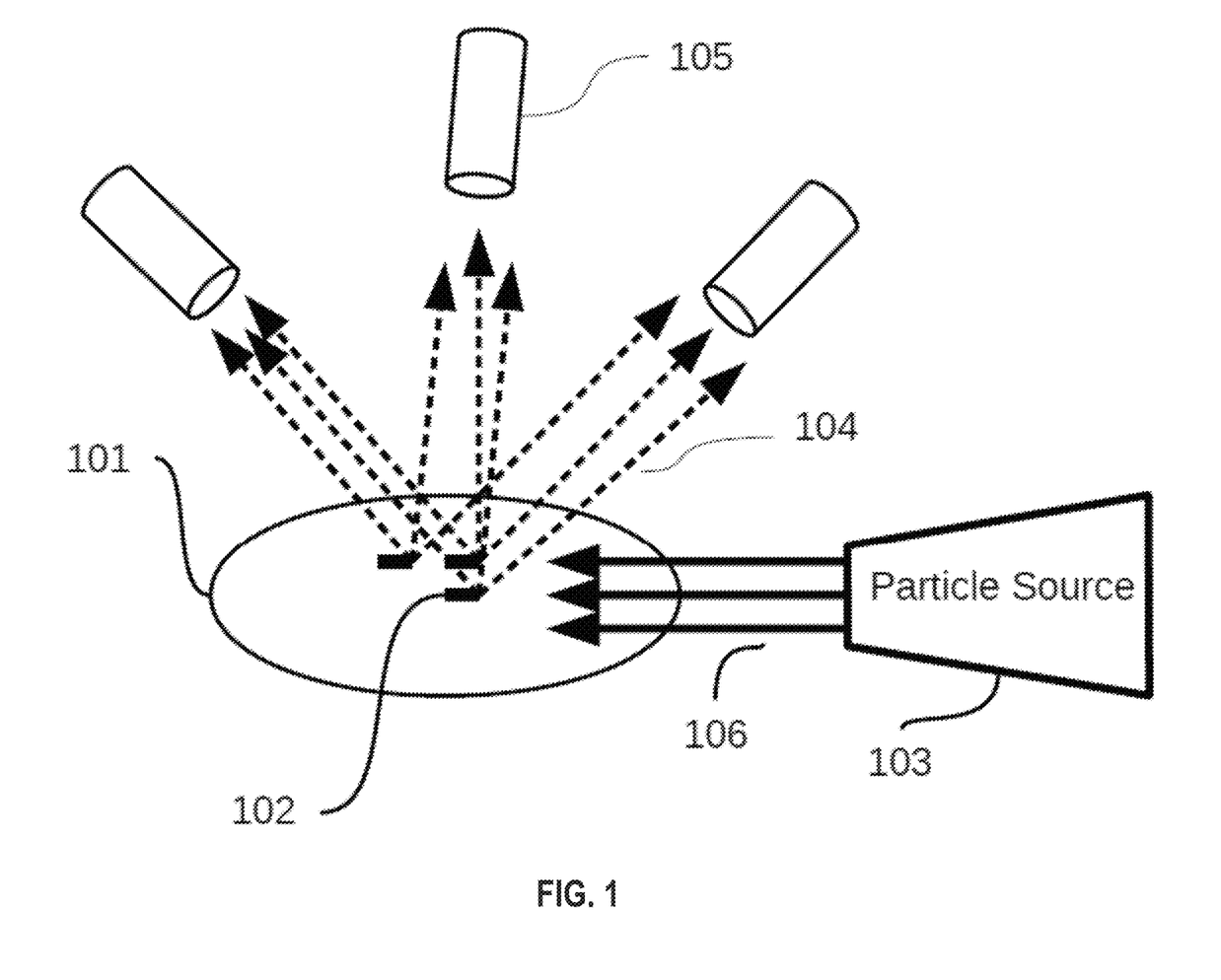
FIG. 1 is a schematic view of an apparatus according to an embodiment of the invention.

FIG. 1 is a schematic of one embodiment of the disclosed apparatus. A source of high energy charged particles 103 produces a beam of particles 106, which is directed at a target 101. In a preferred embodiment, the charged particles are protons with energy ranging from 50 MeV to 250 MeV, but other charged particles and energy ranges may be used.

For example, the method is suited to be used with helium and carbon atom particle beams, both of which are used in practice for medical treatment.

The target 101 contains one or more, e.g., plurality, of fiducial markers 102 which are placed at fixed locations within the target. In the embodiment in which the target is a patient, these fiducial markers may preferably be clinically approved seeds manufactured from gold, with dimensions of approximately 1 mm diameter, as commonly used for prostate implant radiotherapy. One example type of suitable gold fiducial marker is the Visicoil™, which can range in diameter from 0.35 mm to 1.10 mm and length from 0.5 cm to 3 cm. Other suitable markers include gold markers used to define tumor locations with the Cyberknife™ radiosurgery system (wherein the gold markers are 0.8 mm×5 mm in size), and surgical clips used to mark tumor boundaries.

In the embodiment in which the target is a phantom, the fiducial markers may also be composed of gold wire, with preferable dimensions of 1 mm diameter by 5 mm length.

The incident charged particle beam may be directed towards the target and the fiducial markers, with an energy that changes as a function of time in a known way. The control of particle beam energy is a requirement of particle radiotherapy, and the means to accomplish this are well known to practitioners of the art.

When the energy of the particle beam 106 is sufficiently high enough, the Bragg peak will approach the location of the fiducial markers 102, which will begin to produce fluorescence radiation 104.

The fluorescent radiation emitted by the fiducial markers contains one or more identifiable core-level x-ray emission peak characteristic of the atomic composition of the fiducial. In some embodiments, a major elemental component of the fiducial marker is gold (Au), which emits K shell fluorescent x-rays in the range of approximately 68-80 keV, which are sufficient to travel through the target to reach the detectors 105 without excessive attenuation. In some embodiments, both K and L shell fluorescence from Au (gold) fiducials is used.

The fluorescent radiation 104 is not directed into any specific direction. To efficiently collect the radiation, a plurality of x-ray detectors 105 (e.g., multi-energy detectors) can be arranged around the target. In FIG. 1 three such detectors are shown, but more or fewer detectors can be used.

In some embodiments the detector 105 is a scintillation detector, but other detectors of x-ray radiation are known to practitioners skilled in the art and can be used herein. These include solid state energy dispersive detectors, commonly called silicon (Si) and germanium (Ge) detectors, proportional counters, gas-electron multiplier detectors, energy-dispersive detectors, and wavelength dispersive detectors.

The detector 105 produces one or more electrical signals whose amplitude is proportional to the energy of the x-ray 104 that reaches the detector. To enhance the signal-to-noise ratio, pulse-height analysis may be used on the detector signal to isolate the signal from the x-rays originating from the fiducial markers. The fiducial markers produce characteristic x-rays which are sufficiently far from the x-rays produced by other materials in the patient or the phantom, that there is little interference to the desired fiducial signal from other materials.

Figure 2:
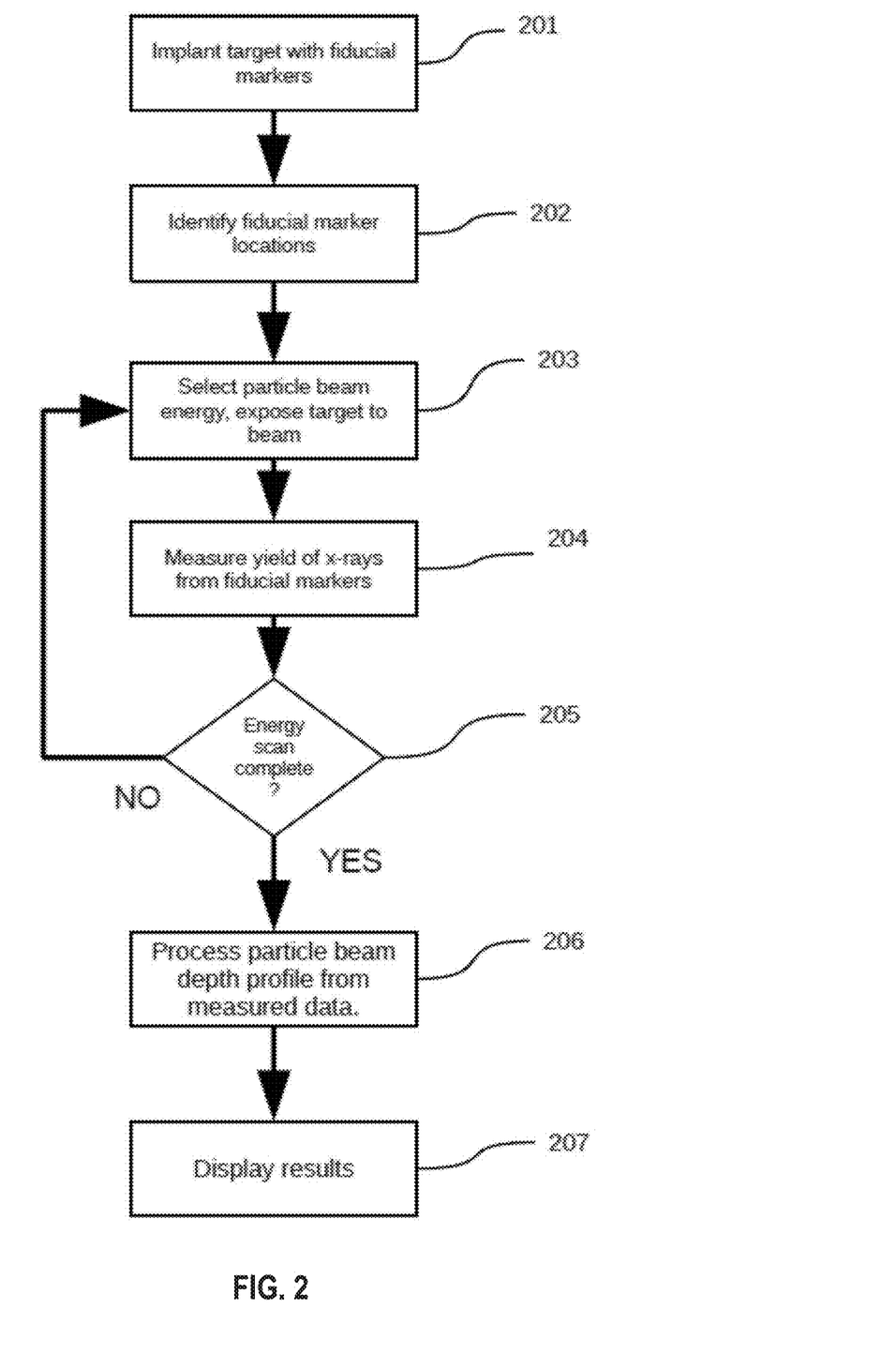
FIG. 2 is a table illustrating steps of a method in accordance with an embodiment of the current invention.

FIG. 2 is a diagram illustrating steps of one embodiment of the disclosed methods. The method can begin with the implantation of fiducial markers in the target, 201. In some embodiments, the target is either a patient, or a phantom selected for quality-assurance of the charged-particle treatment beam 103-106. In the embodiment in which the target is a patient, the fiducial markers may be similar to those already in clinical use for treatment of prostate cancer or lung cancer.

The location of the fiducial markers is identified in the next step of the method, 202. In the case in which the target is a phantom, the location of the markers may be accomplished by the construction of the phantom, or by optical means, or other means well-known to those practiced in the art. In the case in which the target is a patient, the fiducial markers by be localized using an x-ray computed-tomography (CT) scan. Other methods of localizing the fiducial markers, such as radiography, radio-frequency emitters coupled to fiducials, magnetic resonance imaging, or ultrasound, may also be used.

The particle beam 106 may be prepared at a specific energy, and directed at the target, step 203. The yield of fiducial marker fluorescence x-rays can be measured 204 and recorded. Optionally, two or more fluorescent energies are detected to correct for attenuation as described above. The energy of the beam 106 can be incremented, resulting in a stepwise variation of the beam energy with time, with the precise relationship of time and beam energy being known. The beam energy can be compared to the desired endpoint, 205, and the cycle of measurement of x-rays and incrementing beam energy (203, 204, 205) can be repeated until the entire range of particle energies is scanned.

An algorithm 206 can be applied to the measured fluorescence data as a function of time, to determine the precise time at which the particle beam reached the known location of the fiducial markers. This time in turn can be converted into a beam energy, which was recorded in steps 203-205.

In some embodiments, the algorithm used to process the fluorescence data is based on accurate measurements made with proton beams and fiducial markers in a water-equivalent phantom. From this measurement, a profile can be determined that represents the intensity distribution of fluorescence from the fiducial as the Bragg peak sweeps across the fiducial marker. The specific point in the profile that represents the location of the fiducial can thus be accurately determined. This information can be used by the algorithm to extract the location of the particle beam Bragg peak in the target from the measured intensity of fluorescence x-rays as a function of time.

Figure 3:
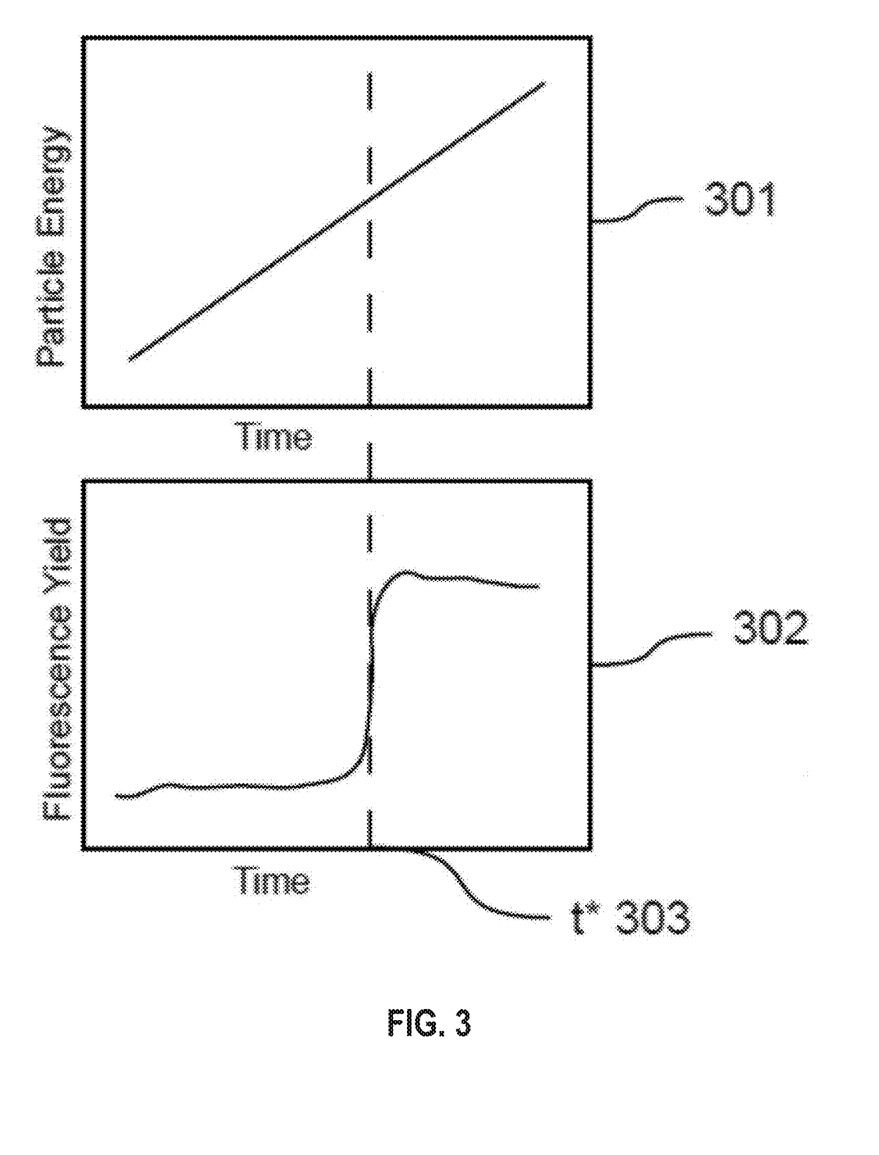
FIG. 3 contains a top graph of model variations of the charged particle beam as a function of time and a bottom graph of the fluorescence yield as a function of time, showing the response of the fiducial marker in accordance with an embodiment of the invention.

As an illustration of the process of the algorithm, FIG. 3 (301) shows a model graph (top) of the variation of the charged particle-beam energy as a function of time, exhibiting a monotonically increasing behavior. The energy of the beam is known at any time. The emitted fluorescence yield from a single fiducial marker is illustrated in the bottom graph of FIG. 3 (302). An edge-like structure occurs at the location of the time t* (303), highlighted by the vertical dashed line. The shape of the edge structure is analyzed to determine the precise time, t*, which corresponds to the particle beam Bragg peak maximum encountering the fiducial marker. Since time also determines beam energy (301), it is then known at which beam energy the particle beam strikes the fiducials.

The results of the algorithm are presented in a suitable form in the final step of the method 207. Specific parts, shapes, materials, functions and modules have been set forth, herein. However, a skilled practitioner will realize that there are many ways to fabricate the disclosed system, and that there are many parts, components, modules or functions that may be substituted for those listed above.

Also disclosed are method of treating a tumor in a subject that involve implanting fiducial markers in or near the cancer, determining charged-particle beam trajectories through the use of a variation of the charged-particle beam energy as a function of time, measurement of the yield of fluorescent radiation from the fiducial markers as a function of time, using an algorithm to optimize beam trajectory, and using the optimized charged-particle beam to irradiate the cancer. Any tumor, e.g., cancer, that can be treated by charged-particle beam radiotherapy can be treated by this optimized method. For example, the cancer can be lung, prostate, breast, skull base tumors, or uveal melanomas. In some embodiments, the fiducial markers are placed at around the tumor margins, at one or more locations inside the tumor, or a combination thereof.

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "tumor" or "neoplasm" refers to an abnormal mass of tissue containing neoplastic cells. Neoplasms and tumors may be benign, premalignant, or malignant. The term "cancer" refers to a cell that displays uncontrolled growth, invasion upon adjacent tissues, and often metastasis to other locations of the body.

While the above detailed description has shown, described, and pointed out the fundamental novel features of the invention as applied to various embodiments, it will be understood that various omissions and substitutions and changes in the form and details of the components illustrated may be made by those skilled in the art, without departing from the spirit or essential characteristics of the invention.

EXAMPLES

Figure 4:
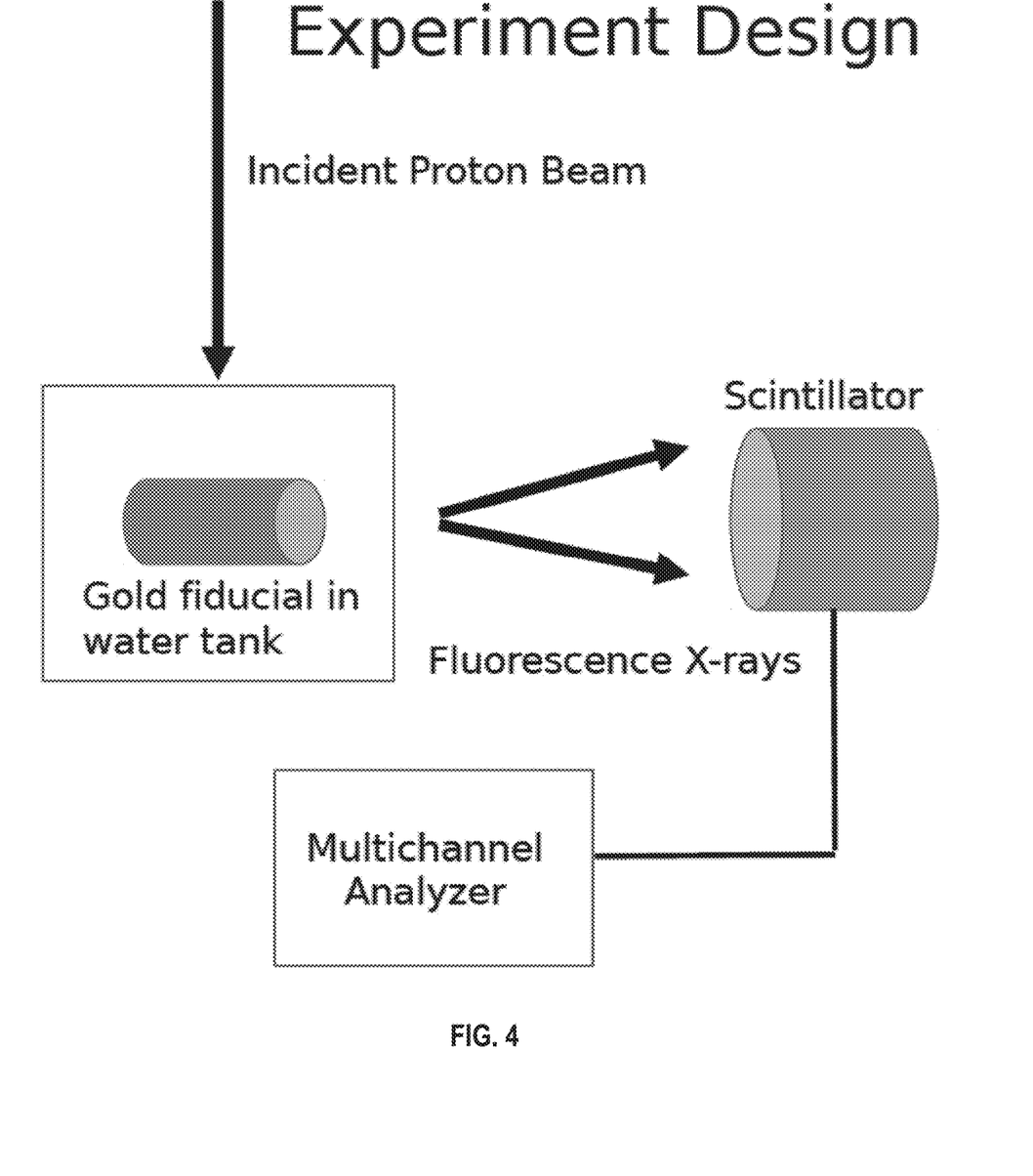
FIG. 4 is a schematic of an experimental design to determine whether proton-induced x-ray fluorescence can be utilized to determine clinically important dosimetric parameters during a proton therapy treatment.

Example 1: Proton Induced X-Ray Fluorescence for In-Vivo Determination of Proton Range and Energy FIG. 4 illustrates the experimental design used to determine whether proton-induced x-ray fluorescence can be utilized to determine clinically important dosimetric parameters during a proton therapy treatment.

Measurements. Therapeutic beams from the UF Proton Therapy Institute were used to excite proton induced x-ray fluorescence emission (PIXE) from cylindrical pure gold fiducial markers. The markers were embedded in a homogeneous water phantom and PIXE was measured using NaI scintillators with energy dispersive spectral analysis. The geometry of the phantom and marker placement was chosen to model parallel-opposed beam treatment of prostate cancer by proton therapy.

Modelling. An analytical model of fluoescence yield in realistic therapy conditions was developed using semi-empirical Au K and L shell cross-sections for proton induced emission, and attenuation data for both xray channels. The fluorescence yield from these markers was further modeled using the GEANT4 Monte-Carlo package with low-energy corrections.

Figure 5:
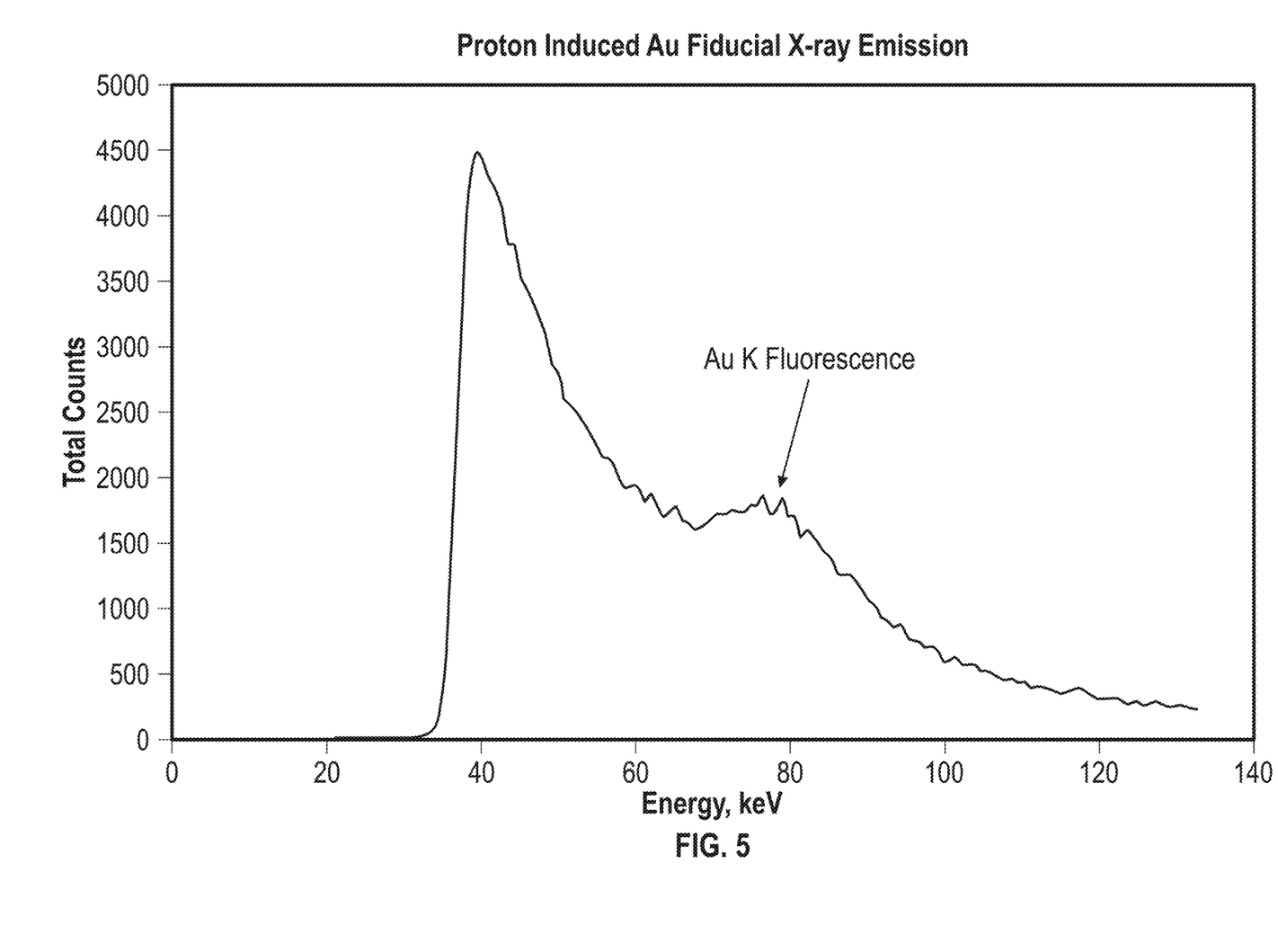
FIG. 5 is a graph showing pulse height analysis of proton induced Au fiducial x-ray emission (counts as a function of energy, keV).

Measurements were made with proton beam maximum energy ranging from 80 MeV to 200 MeV. The pure gold fiducial was placed at a fixed depth in a water tank. The gold K and L shell x-rays passed through 13.5 cm of water and the wall of the acryllic tank before reaching a 2 cm diameter NaI scintillator where they were detected and energy scaled using pulse height analysis (FIG. 5).

Backgrounds were taken with no beam and no gold sample, and with a proton beam but no gold sample. The pulse-height analysis spectrum was accumulated in a multichannel analyzer, and calibrated using a Cs-137 source.

Figure 6:
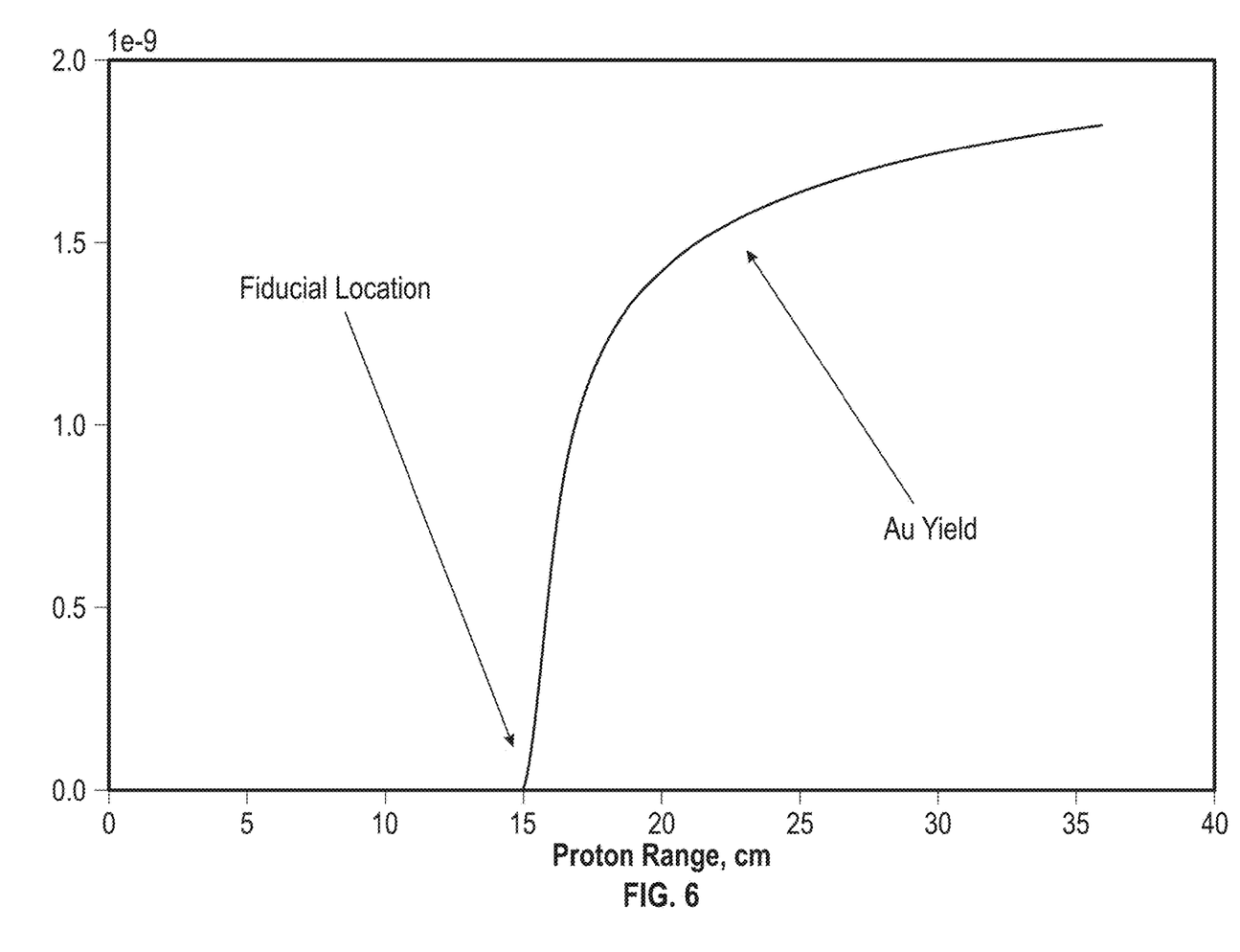
FIG. 6 is a graph showing analytical model of the experiment using Bragg curve approximations with stopping power parameters for Au adapted from NIST data tables (fluorescence as a function of path length, cm).

An analytical model of the experiment was developed using the Bragg curve approximations of Bortfeld [Med. Phys. 24 (1997) 2024-2033] with stopping power parameters for Au adapted from NIST data tables (FIG. 6). The model incorporates range straggling and energy spread, and fluence reduction due to inelastic nuclear events, using a parameterization to fit data of Janni [At. Data Nucl. Data Tables 27 (1982) 147-339].

PIXE from gold fiducial markers was readily detected above background using conventional NaI-Tl scintillation detectors, in a clinical therapy proton beam. This work shows the feasibility of using PIXE for in-vivo dosimetry with proton therapy.

A number of embodiments of the invention have been described. Nevertheless, it will be understood that various modifications may be made without departing from the spirit and scope of the invention. Accordingly, other embodiments are within the scope of the following claims.

What is claimed is:

1. A method for improving accuracy of a charged-particle beam used in cancer therapy, the method comprising:
    providing a plurality of fiducial markers that emit fluorescent x-rays of distinct energies when struck by the charged-particle beam, wherein the plurality of fiducial markers are adapted to be implanted in a subject;
    determining a location of each of the plurality of fiducial markers after being implanted into the subject;
    operating a source of charged particles to deliver the charged-particle beam toward the subject, wherein an energy level of the charged-particle beam is incrementally increased as a function of time;
    measuring, using a plurality of fluorescent energy detectors, energy levels of the fluorescent x-rays emitted by the plurality of fiducial markers responsive to the subject being struck by the charged-particle beam as a function of time corresponding to the incremental increase of the energy level of the charged-particle beam, wherein the plurality of fluorescent energy detectors generate signals having an amplitude proportional to the energy levels of the fluorescent x-rays;
    determining a penetration of the charged-particle beam in the subject based on the energy level of the charged-particle beam and the energy levels of the fluorescent x-rays as measured; and
    presenting an indication of the penetration of the charged-particle beam in the subject on a display.

2. The method of claim 1, wherein the plurality of fiducial markers comprise a first material that produces a first fluorescent x-ray having an energy ranging from 20 keV to 150 keV.

3. The method of claim 2, wherein the first material is gold (Au).

4. The method of claim 2, wherein the plurality of fiducial markers include a second material that produces a second fluorescent x-ray having an energy ranging from 20 keV to 150 keV, wherein the energy of the second fluorescent x-ray is distinct from the energy of the first fluorescent x-ray.

5. The method of claim 4, wherein each of the plurality of fiducial markers includes a greater amount of the first material than the second material.

6. The method of claim 1, wherein the plurality of fluorescent energy detectors are scintillation detectors.

7. The method of claim 1, wherein the plurality of fiducial markers comprise a material that, upon being struck by the charged-particle beam, emits fluorescent x-rays that are distinct from radiation not originating from the plurality of fiducial markers.

8. The method of claim 1, wherein the energy level of the charged-particle beam ranges from 50 MeV to 250 MeV.

9. The method of claim 1, wherein the penetration of the charged-particle beam in the subject is calculated by comparing a Bragg peak of the charged-particle beam to the energy levels of the fluorescent x-rays.

10. The method of claim 1, further comprising performing a pulse-height analysis on the signals generated by the plurality of fluorescent energy detectors to isolate the signals associated with energy levels of the charged-particle beam from the fluorescent x-rays originating from the plurality of fiducial markers.

11. The method of claim 1, wherein the location of each of the plurality of fiducial markers after being implanted into the subject is determined using x-ray computed tomography (CT), radiography, magnetic resonance imaging (MRI), or ultrasound.

12. The method of claim 1, wherein determining the location of each of the plurality of fiducial markers after being implanted into the subject comprises generating a spatial map using a medical imaging device, wherein the spatial map that indicates the location of each of the plurality of fiducial markers within the subject.

* * * * *